(12) United States Patent
Trunin et al.

(10) Patent No.: US 9,216,184 B1
(45) Date of Patent: Dec. 22, 2015

(54) AGENT AND METHOD FOR INCREASING TESTOSTERONE LEVEL IN A BODY

(71) Applicant: Lunada Biomedical, LLC, Los Angeles, CA (US)

(72) Inventors: Roman Anatolievich Trunin, Moscow (RU); Evgenii Iljich Maevskii, Pushino (RU); Mikhail Lvovich Uchitel, Mytishi (RU)

(73) Assignee: Lunada Biomedical, LLC, Los Angeles, CA (US)

( * ) Notice: Subject to any disclaimer, the term of this patent is extended or adjusted under 35 U.S.C. 154(b) by 0 days.

(21) Appl. No.: 14/280,571

(22) Filed: May 17, 2014

Related U.S. Application Data

(60) Provisional application No. 61/834,453, filed on Jun. 13, 2013.

(51) Int. Cl.
| | |
|---|---|
| *A61K 31/593* | (2006.01) |
| *A61K 31/194* | (2006.01) |
| *A61K 31/315* | (2006.01) |
| *A61K 31/198* | (2006.01) |
| *A61K 31/375* | (2006.01) |
| *A61K 31/197* | (2006.01) |
| *A61K 31/355* | (2006.01) |

(52) U.S. Cl.
CPC ............. *A61K 31/593* (2013.01); *A61K 31/194* (2013.01); *A61K 31/197* (2013.01); *A61K 31/198* (2013.01); *A61K 31/315* (2013.01); *A61K 31/355* (2013.01); *A61K 31/375* (2013.01)

(58) Field of Classification Search
CPC .................................................... A61K 31/593
See application file for complete search history.

(56) References Cited

PUBLICATIONS www.herbal-supplement-resource.com (internet archive 2008).*
Progene product page (internet archive May 25, 2010).*
Virectin product page (internet archive 2010).*

* cited by examiner

*Primary Examiner* — Paul Zarek
(74) *Attorney, Agent, or Firm* — Bardmesser Law Group

(57) ABSTRACT

A composition for regulating male sexual function includes at least one amino acid selected from a group consisting of L-Glutamic acid (glutamate), L-Arginine, glycine, L-aspartate, L-carnitine, L-tyrosine, L-glutamine and/or its pharmaceutically acceptable salt, such as any of monosodium-L-glutamate monogidrate, L-potassiumarginine, L,-ammoniumaspartate, L-arginine HCl, sodium-L-tyrasine, lithium aspartate, in the amount of 1-1000 mg, preferably 10-300 mg; at least one vitamin, in the amount of 1-500% of a daily recommended dose, preferably 10-200%; and at least one chelated compound of a formula: acid-Me-acid.$nH_2O$, wherein Me is a metal chosen from any of Ca, Mg and Zn, wherein the acid is a dicarboxylic acid anion chosen from the group consisting of succinic acid, fumaric acid or aspartic acid, and wherein n=0-8. The composition increases testosterone level in a body of a male mammal.

15 Claims, No Drawings

AGENT AND METHOD FOR INCREASING TESTOSTERONE LEVEL IN A BODY

CROSS-REFERENCE TO RELATED APPLICATIONS

This application is a non-provisional of U.S. Provisional Patent Application No. 61/834,453, filed on Jun. 13, 2013, which is incorporated by reference herein.

BACKGROUND OF THE INVENTION

1. Field of the Invention

The invention relates to medicine and to therapeutic-prophylactic nutrition, and more particularly, to biologically active additives to food and to compounds that normalize function of the reproductive organs, and to restoring testosterone level in the body that is lowered due to different types of sexual and metabolic disorders, such as hypogonadism.

2. Description of the Related Art

Two conventional methods are widely known to prevent and treat sexual and metabolic disorders:

treatment with hormonal compounds, primarily by testosterone injections, and treatment with infusions and extracts of plant origin.

Also, a use of vasodilators as a method that permits a certain increase in hormonal background, combined with restoration of erectile function by itself and combined with prehormones of plant origin, has become increasingly popular in recent years.

Sexual function is an important component of the reproductive system of the body, since normal sexual functioning of the body is often psychologically much more important for men than for women. In developed countries, the frequency of sexual disorders among men is steadily increasing, which dictates the need to investigate the mechanisms of normal or altered sexual function (WHO, 2004).

Male reproductive function of the body is subject to influence of different ecological, chemical, physical and biological factors, such as heredity, environment and stress. Many factors lead to a reduction in testosterone production. However, psychological factors also lead to a significant degree to a reduction in testosterone level. Dysregulation of central mechanisms that play a critical role in the development of sexual motivation, on which sexual function depends, is the reason for most disorders in male sexual function.

Synthesis of testosterone is ultimately a complex integrative process consisting of central motivational and peripheral copulatory mechanisms. The mechanisms that regulate sexual function are ensured to a significant degree by neuronal processes of the preoptic zone of the hypothalamus, which are activated by different neuromediator systems—dopamine (DA), acetylcholine (AC), 5-hydroxytryptamine (5-HT), and noradrenaline (NA) (Bitran, 1987; Dorner, 1989; Gladkova, 2000).

Treatment of testosterone deficiency by testosterone injections began about 50 years ago. Originally, an attempt was made to create drug forms of the noninjection type, but two problems were discovered. The first is that testosterone is unstable during storage, and the second is that testosterone is introduced to the body through the nasal mucosa or by being taken internally through the stomach. Treatment of impotence and partially male infertility, even today, is accomplished by testosterone injections, but this method has a number of limitations and problems. First, the tolerability of such injections is low. Only a third of patients tolerate the injections without discomfort, and a quarter of the patients cannot tolerate it because of pain. Second, the effectiveness of such injections is short-lived, at most a few hours. Third, resistance gradually develops, which requires an increase in therapeutic dose. For this reason, the search for a safe and effective means to restore the free testosterone level in males is still very important.

The most widely used method at present for increasing testosterone level is the creation of compositions based on plant extracts that include prehormonal compounds, different phytosteroids and specific alkaloids. Such compositions come from traditional medicine: ancient Chinese, Himalayan and Ayurvedic. Modern agents have been optimized according to composition of the extracts, production technology, dosage and determination of the activity of the active ingredients. Compound based on Testofen (Trigonella foenum-graecum), an extract obtained microbiologically, is the most widespread today. It is based on a broad spectrum of steroids, prehormones and glycosides. These compounds include Vitaly-T-Aid (composition: Testofen 600 mg, Male Wellness blend 100 mg, saw *palmetto* berry powder, astragalus root powder, phytosterol, Asian ginseng root powder, tribulus fruit extract, L-arginine), T Strong (composition: LJ100® Long Jack, L-arginine, L-citrulline, β sitosterols) and others.

This group includes the compound Tribestan that has recently become common in Europe, whose active ingredients are steroid saponins of the furastanol type, among which protodioscin predominates, obtained from the above-ground part of *Tribulus terrestris* L. (devil's thorn). This year-around plant is found throughout the world.

Two factors are the main shortcomings of these agents. First, these agents do not eliminate (even partially) the reason for development of testosterone deficiency. Rather, they only partially unload the actual organ mechanisms of hormonal synthesis, and second, they do not ensure a prolonged effect, especially after termination of taking of the compound.

As a rule, testosterone deficiencies are accompanied by a reduction in erectile function, for which reason there are number of studies based on the vasodilatory of a number of compounds, see EP 0463450 (Vasoactive intestinal polypeptide analogues and use thereof), EP 1041880 (Administration of arginine to warm cool/cold tissue), U.S. Pat. No. 6,458,841 (Topical and oral delivery of arginine to cause beneficial effects). A combination of vasodilators with prehormones of plant origin increased the effectiveness of these compounds, but did not solve the problems described above.

The compound closest in effect to the compound according to the invention (and only partially in terms of composition) is the compound Progene with the composition: Nugenix testosterone complex, Zn, B6, B12. Nugenix testosterone complex is the commercial name of the mixture of three components. Testofen—source of prehormones and steroids, L-citrulline malate-arginine precursor, which ensures activation of vasodilatory processes in the body, *Tribulus terrestris*—source of natural saponin steroids. This combination proved to be very effective, but this compound also does not have a prolonged effect and does not ensure stable remission of the mechanisms of testosterone production. However, like any source of steroids, when taken chronically, it causes an entire series of functional disorders in the body.

Thus, the question of how to enhance active testosterone synthesis in the body for a prolonged period, without hormones and steroids, remains to be solved.

DETAILED DESCRIPTION OF THE PREFERRED EMBODIMENTS

Reference will now be made in detail to the preferred embodiments of the present invention.

The objectives of the invention are achieved in that, in addition to amino acids and/or their salts and vitamins, the proposed agent contains at least one chelated salt of a dicarboxylic acid of the general formula acid-Me-acid.$nH_2O$, where Me is a metal chosen from the group: Ca, Mg, Zn, and acid is a dicarboxylic acid anion chosen from the group: succinic and/or fumaric and/or aspartic acid, n=0-8. In addition to these components, the agent can contain an ammonium salt of a dicarboxylic acid chosen from the group: succinic and/or fumaric acid. The proposed agent can be prepared in the form of tablets, capsules, granules, aqueous or oil suspension, and/or powder. Sugars, starches, microcelluloses, lactate, casein and/or their mixtures can be used in compound of tablets or granules.

The proposed agent can be used for treatment of sexual disorders associated with a reduction in the level of testosterone production, including hypogonadism, both in a single administration and with a course of treatment.

Hypogonadism is one of the most difficult pathologies for treatment. Generally, it is very difficult to raise the testosterone level significantly in hypogonadic males, even with testosterone injections. The proposed method and composition raises endogenic testosterone levels to physiologically acceptable ones for all pathologies, even for hypogonadism.

All the substances that form parts of the compound are vitamins, basic metabolites, amino acids or their derivatives and are safe for nutritional use.

The original research that led to the discovery of the present compositions was directed to regulating heart activity and possible reduction in arterial blood pressure. The inventors were looking for compounds that support effective transport of magnesium ions and also support the energetic functions of cardiac mitochondria. Hypertensive rats of the Wistar line, age 16-20 months, were used as a model. The originally composition included magnesium succinate tetrahydrate, MSG, L-arginine, glycine, vitamins C and E. However, no noticeable reduction in arterial blood pressure was found. Surprisingly, however, the behavior of male rats changed visibly. Male rats began exhibits a higher level of aggression, as well as a higher level of motion. The increase in the activity and aggression corresponded to transporting the animals to a different part of the lab for taking samples for analysis. Observation showed that this occurs when the males are within smell contact with young female rats. A further unexpected effect was discovered—the older male rats were behaving in a manner very similar to young male rates when it came to their reproductive function. Further investigation confirmed that the proposed compounds are, surprisingly, highly effective for increasing testosterone levels in mammals.

The invention is illustrated, but not limited, by the following examples.

Example 1

The agent Progene, available without prescription, was used to investigate the effect on blood free testosterone level. According to the manufacturer, one of the main effects of the product is an increase in free testosterone level of the blood. The composition is: Nugenix testosterone complex, Zn, B6, B12. According to the manufacturer, Progene contains L-arginine HCl—1000 mg, Tongkat ali 50:1, extract (*Eurycoma longifolia* jack) (root)—60 mg, DHEA (dehydroepiandrosterone)—50 mg, Guarana seed extract—10 mg, Progene™ Proprietary Blend—200 mg.

Progene contains L-arginine HCl, zinc salt, vitamins, prehormonal components of plant origin (pretestosterones) and the hormone dehydroepiandrosterone. Note that L-arginine can vary widely in such formulations, in a range 10-3000 mg/dose, vitamins from 0.5% to 1000% of the daily dose.

The testosterone complex consists of Testofen, an extract of plant origin, which is a testosterone precursor. Its presence increases free testosterone production. L-Citrulline malate, which is an L-arginine precursor, and *Tribulus terrestris*, a plant extract containing steroids of the saponin class, which increase testosterone synthesis activity in the body, are also used in the complex. In addition, both extracts are a source of readily available amino acids and trace elements.

The acquired product was then used in preclinical and clinical studies.

Example 2

A mixture of acid magnesium fumarate tetrahydrate with glutamic acid, hydrated zinc succinate, L-arginine and ascorbic acid (vitamin C) was prepared in a mixer. Tablets weighing 300 mg were pressed by direct dry pressing from the obtained mixture. The composition of the tablet is shown in Table 2.

TABLE 2

| Composition | Weight of component |
| --- | --- |
| Magnesium fumarate tetrahydrate, mg | 40 |
| Glutamic acid, mg | 140 |
| Zinc succinate hydrate, mg | 60 |
| L-Arginine, mg | 40 |
| Vitamin C | 20 |
| Total | 300 mg |

The compound can contain Magnesium fumarate tetrahydrate 1-5000 mg (optimal range 10-400 mg), Zinc succinate hydrate 1-5000 mg (optimal range 10-400 mg), Glutamic acid 1-1000 mg (optimal range 10-300 mg), L-Arginine 1-1000 mg (optimal range 10-300 mg), Vitamin C 0.000001-100 mg (optimal range 0.0001-50 mg).

Magnesium fumarate tetrahydrate can be replaced with magnesium succinate semihydrate (0.5 $H_2O$) in the amount of 20-100 mg, or with magnesium aspartate in the amount of 10-60 mg, or with calcium succinate trihydrate in the amount of 40-500 mg. (Numerous other such hydrates are also possible, at least in theory, and they are all described with the general formula acid-Me-acid.$nH_2O$). Zinc succinate hydrate can be replaced with Zinc fumarate in the amount of 5-150 mg, calcium succinate dehydrate in the amount of 40-200 mg, calcium fumarate in the amount of 20-100 mg and so on. Aminoacids can be selected from: L-Glutamic acid (glutamate), L-Arginine, glycine, L-aspartate, L-carnitine, L-tyrosine, L-glutamine (or their salts) in the amount of 10-1000 mg. Vitamin C can be replaced with 3-15 mg of vitamin E, or with 0.2-5 mg vitamin $B_1$, or with 1-10 μg vitamin $D_3$, or with 0.5-10 mg vitamin $B_6$ The obtained tablets were then used for preclinical and clinical studies.

Example 3

A mixture of magnesium fumarate tetrahydrate with sodium mono L glutamate monohydrate, calcium succinate, L-arginine, L carnitine, vitamin E and ascorbic acid (vitamin C) was prepared in a mixer of a tumbler type. Premixes weighing 220 mg (including 20 mg fructose precipitated in the mixture) were formed from the obtained mixture by the dry-wet method in 8% aqueous fructose solution. The obtained premixes were coated according to a standard method into a mixture containing corn starch, fructose, microcrystalline cellulose and food dye. The composition of the premix is shown in Table 3.

TABLE 3

| Composition | Weight of component |
| --- | --- |
| Magnesium fumarate tetrahydrate, mg | 20 |
| Calcium succinate, mg | 70 |
| Sodium mono-L-glutamate monohydrate, mg | 30 |
| L-Arginine, mg | 40 |
| L-Carnitine, mg | 10 |
| Vitamin C, mg | 20 |
| Vitamin E (tocopherol acetate on a support 50 wt %), mg | 10 |
| Fructose, mg | 20 |
| Total | 220 mg |

The compound can contain Magnesium fumarate tetrahydrate 1-5000 mg (optimal range 10-400 mg), Calcium succinate hydrate 1-5000 mg (optimal range 10-400 mg), Sodium mono-L-glutamate monohydrate 1-1000 mg (optimal range 10-300 mg), L-Arginine 1-1000 mg (optimal range 10-300 mg), L-Carnitine 1-1000 mg, (optimal range 10-300 mg), Vitamin C 0.000001-100 mg (optimal range 0.0001-50 mg), Vitamin E 0.000001-100 mg (optimal range 0.0001-50 mg). Fructose is not an active component, there is no particular restriction on its amount.

Magnesium fumarate tetrahydrate can be replaced with magnesium succinate semihydrate (0.5 $H_2O$) in the amount of 20-100 mg, or magnesium aspartate in the amount of 10-60 mg, or calcium succinate trihydrate in the amount of 40-500 mg. (more generally, with a hydrate of the formula acid-Me-acid.$nH_2O$). Calcium succinate hydrate can be replaced with Zinc fumarate in the amount of 5-150 mg, Zinc succinate dehydrate in the amount of 40-200 mg, calcium fumarate in the amount of 20-100 mg and so on. Aminoacids can be selected from: L-Glutamic acid (glutamate), L-Arginine, glycine, L-aspartate, L-carnitine, L-tyrosine, L-glutamine (or their salts, for example, Sodium mono-L-glutamate monohydrate вместо L-glutamate) in the amount of 10-1000 mg. Vitamin C can be replaced with 0.2-5 mg vitamin $B_1$, or with 1-10 µg vitamin $D_3$, or with 0.5-10 mg vitamin $B_6$. Vitamin E can be replaced with 0.2-5 mg vitamin $B_1$, or with 1-10 µg vitamin $D_3$, or with 0.5-10 mg vitamin $B_6$, or with 10-2000 µg vitamin $B_9$ (folic acid). More generally, 1-500% of the recommended daily dose of the vitamins can be used, based on WHO recommendations, preferably 10-200%.

The obtained coated tablets were then sent for preclinical and clinical studies.

Example 4

A mixture of glycine, acid zinc fumarate was prepared, carefully mixed, screened and then tocopherol acetate (vitamin E) and vitamin D3 were slowly added to the mixture, whereupon the obtained mixture was mixed in a mixer of the tumbler type. Previously screened sodium mono-L-glutamate, calcium succinate, magnesium succinate and L-arginine were mixed into the obtained mixture. Mixture no. 1 was obtained.

Ammonium succinate was mixed separately in a mixer with ascorbic acid (vitamin C) and a finished mixture no. 2 was obtained. Mixture no. 1 and mixture no. 2 were separately encapsulated in size 3 capsules on an automatic capsule machine, producing a group of two capsules.

The compositions and weights are shown in Table 4.

TABLE 4

| Composition, mg | Capsule no. 1 (yellow) |
| --- | --- |
| Calcium succinate | 85 |
| Magnesium succinate | 18 |
| Zinc fumarate | 15 |
| L-Arginine | 15 |
| Glycine | 15 |
| Sodium mono-L-glutamate | 40 |
| Vitamin E (8 mg + 2 mg support, form E90) | 10 |
| Vitamin D3 (2 µg in 2 mg support) | 2 |
| Total | 200 mg |
| Capsule no. 2 (white) | |
| Vitamin C | 20 |
| Ammonium succinate | 180 |
| Total | 200 mg |

The composition can contain Magnesium succinate 1-5000 mg (optimal range 10-400 mg), calcium succinate 1-5000 mg (optimal range 10-400 mg), Zinc fumarate 1-5000 mg (optimal range 10-400 mg), sodium mono-L-glutamate 1-1000 mg, (optimal range 10-300 mg), L-Arginine 1-1000 mg (optimal range 10-300 mg), Glycine 1-1000 mg (optimal range 10-300 mg), Vitamin C 0.000001-100 mg (optimal range 0.0001-50 mg), Vitamin E 0.000001-100 mg (optimal range 0.0001-50 mg), Vitamin D3 0.000001-0.01 mg, Ammonium succinate 0-5000 mg (optimal range 20-400 mg).

Magnesium succinate can be replaced with magnesium fumarate hydrate in the amount of 20-100 mg, or with magnesium aspartate in the amount of 10-60 mg, or with calcium succinate trihydrate in the amount of 40-500 mg, or with zinc aspartate hydrate in the amount of 30-100 mg (more generally, a hydrate of the formula acid-Me-acid.$nH_2O$). Calcium succinate can be replaced with Zinc fumarate in the amount of 5-150 mg, Zinc succinate dihydrate in the amount of 40-200 mg, calcium fumarate in the amount of 20-100 mg and so on. Zinc fumarate can be replaced with Zinc succinate hydrate in the amount of 10-60 mg, or with Zinc aspartate trihydrate in the amount of 10-100 mg.

Aminoacids can be selected from: L-Glutamic acid (glutamate), L-Arginine, glycine, L-aspartate, L-carnitine, L-tyrosine, L-glutamine (or their salts, e.g., Sodium mono-L-glutamate monohydrate instead of L-glutamate) in the amount of 10-1000 mg. Vitamin C can be replaced with 0.2-5 mg vitamin $B_1$, or with 1-10 µg vitamin $D_3$, or with 0.5-10 mg vitamin $B_6$. Vitamin E can be replaced with 0.2-5 mg vitamin $B_7$, or with 1-10 μg vitamin $D_3$, or with 0.5-10 mg vitamin $B_6$, or with 10-2000 μg vitamin $B_9$ (folic acid). Ammonium succinate can be replaced with Ammonium fumarate in the amount of 60-120 mg, or with a mixture of 50-150 mg Ammonium succinate, with 15-100 mg Ammonium fumarate, or with 10-300 mg monoammonium succinate.

The obtained capsules were then sent for preclinical and clinical studies.

Example 5

Male rats of the Wistar strain were used to conduct preclinical studies on animals. Some of the animals were subjected to operation beforehand (one testicle was removed) before sexual maturity arrived—i.e., with hypogonadal animals. Eighteen groups of 12 male rats each were then formed:

Control (K)—control group, intact animals.

Negative control (KN)—group of hypogonadal rats.

Experimental (EXN1) group—a group of intact animals who received the agent according to example 1 for 10 days in an amount of 20 mg/kg of weight once a day.

Experimental group (EXG1)—a group of hypogonadal males who received the agent according to example 1 for 10 days in an amount of 20 mg/kg of weight once a day.

Experimental group (EON1)—a group of intact animals who received the agent according to example 1 once in an amount of 80 mg/kg of weight once a day.

Experimental group (EOG1)—a group of hypogonadal rats who received the agent according to example 1 once in an amount of 80 mg/kg of weight once a day.

Experimental group (EXN2)—a group of intact animals who received the agent according to example 2 for 10 days in an amount of 10 mg/kg of weight once a day.

Experimental group (EXG2)—a group of hypogonadal males who received the agent according to example 2 for 10 days in an amount of 20 mg/kg of weight once a day.

Experimental group (EON2)—a group of intact rats who received the agent according to example 2 once in an amount of 80 mg/kg of weight once a day.

Experimental group (EOG2)—a group of hypogonadal rats who received the agent according to example 2 once in an amount of 80 mg/kg of weight once a day.

Experimental group (EXN3)—a group of intact animals who received the agent according to example 3 for 10 days in an amount of 20 mg/kg of weight once a day.

Experimental group (EXG3)—a group of hypogonadal males who received the agent according to example 3 for 10 days in an amount of 20 mg/kg of weight once a day.

Experimental group (EON3)—a group of intact rats who received the agent according to example 3 once in an amount of 80 mg/kg of weight once a day.

Experimental group (EOG3)—a group of hypogonadal rats who received the agent according to example 3 once in an amount of 80 mg/kg of weight once a day.

Experimental group (EXN4)—a group of intact rats who received the agent according to example 4 for 10 days in an amount of 20 mg/kg of weight once a day.

Experimental group (EXG4)—a group of hypogonadal males who received the agent according to example 4 for 10 days in an amount of 20 mg/kg of weight once a day.

Experimental group (EON4)—a group of intact rats who received the agent according to example 4 once in an amount of 80 mg/kg of weight once a day.

Experimental group (EOG4)—a group of hypogonadal rats who received the agent according to example 4 once in an amount of 80 mg/kg of weight once a day.

Administration of the compound was accomplished with a probe in the form of aqueous suspension.

We determined the level of the following hormones in the blood:

Ts—testosterone
E2—estradiol
DHEA—dehydroepiandosterone
PRG—progesterone

Method of determination: The type and amount of corresponding hormone from the investigated serum or calibration sample were determined by bonding with the first monoclonal antibodies to the given hormone. The original monoclonal antibodies were applied to the surface of the well. The second monoclonal antibodies to the hormone conjugated with horseradish peroxidase react with the primary monoclonal antibody. As a result, a complex of the "sandwich" type is formed. The bound substrate (enzyme, hormone) is determined quantitatively by color reaction with a chromogenic substrate. The color intensity is proportional to the concentration of the hormone determined in the sample. The results are calculated automatically with a multichannel recording spectrophotometer at a wavelength of 450 nm.

Blood was collected from the rats from the caudal vein 2 hours after taking the compound during acute single administration.

Blood was taken from the rats during chronic administration before the beginning of administration (day 0), on the 5th and 10th administrations 5 to 7 hours after taking the compound and on the 10th (day 20) and 20th (day 30) day after termination of taking of the compound.

All blood samples for analysis were taken in the interval 7:00 a.m. to 10:00 a.m.

TABLE 5

Level of hormones in the blood in the intact rats during a course of treatment and after termination of taking.

| Group | Day 0 | Day 5 | Day 10 | Day 20 | Day 30 |
|---|---|---|---|---|---|
| Testosterone, nmol/L | | | | | |
| K | 5.81 ± 0.83 | 5.63 ± 1.02 | 5.77 ± 0.61 | 5.87 ± 0.96 | 5.74 ± 0.72 |
| EXN1 | 5.92 ± 0.66 | 5.99 ± 0.72 | 6.15 ± 0.53 | 5.97 ± 0.47 | 5.92 ± 0.60 |
| EXN2 | 5.69 ± 0.68 | 6.60 ± 1.24 | 6.73 ± 0.94 | 6.48 ± 0.90 | 6.16 ± 0.86 |
| EXN3 | 5.84 ± 0.78 | 6.86 ± 1.04 | 6.97 ± 1.09 | 6.52 ± 0.87 | 6.02 ± 0.88 |
| EXN4 | 5.73 ± 0.54 | 6.98 ± 0.83 | 7.22 ± 0.98 | 7.06 ± 0.68 | 6.53 ± 0.40 |
| Progesterone, nmol/L | | | | | |
| K | 4.26 ± 0.26 | 4.51 ± 0.63 | 4.31 ± 0.22 | 4.37 ± 0.36 | 4.29 ± 0.34 |
| EXN1 | 4.57 ± 0.33 | 4.83 ± 0.42 | 4.91 ± 0.26 | 4.65 ± 0.28 | 4.59 ± 0.33 |
| EXN2 | 4.40 ± 0.18 | 5.24 ± 0.36 | 5.41 ± 0.27 | 5.33 ± 0.33 | 5.10 ± 0.42 |

TABLE 5-continued

Level of hormones in the blood in the intact rats during a course of treatment and after termination of taking.

| Group | Day 0 | Day 5 | Day 10 | Day 20 | Day 30 |
|---|---|---|---|---|---|
| EXN3 | 4.27 ± 0.41 | 5.34 ± 0.48 | 5.62 ± 0.42 | 5.38 ± 0.54 | 5.16 ± 0.28 |
| EXN4 | 4.22 ± 0.52 | 5.83 ± 0.68 | 5.90 ± 0.74 | 5.59 ± 0.45 | 5.34 ± 0.38 |
| Estradiol, nmol/L | | | | | |
| K | 0.64 ± 0.05 | 0.65 ± 0.06 | 0.65 ± 0.05 | 0.63 ± 0.05 | 0.65 ± 0.05 |
| EXN1 | 0.67 ± 0.06 | 0.69 ± 0.07 | 0.69 ± 0.07 | 0.67 ± 0.05 | 0.68 ± 0.05 |
| EXN2 | 0.65 ± 0.04 | 0.61 ± 0.06 | 0.61 ± 0.05 | 0.63 ± 0.03 | 0.64 ± 0.05 |
| EXN3 | 0.67 ± 0.06 | 0.59 ± 0.10 | 0.58 ± 0.08 | 0.60 ± 0.06 | 0.62 ± 0.06 |
| EXN4 | 0.68 ± 0.04 | 0.57 ± 0.11 | 0.56 ± 0.10 | 0.56 ± 0.08 | 0.61 ± 0.05 |
| Dehydroepiandosterone sulfate, μg/mL | | | | | |
| K | 0.222 ± 0.012 | 0.224 ± 0.005 | 0.224 ± 0.009 | 0.220 ± 0.010 | 0.224 ± 0.006 |
| EXN1 | 0.218 ± 0.009 | 0.219 ± 0.006 | 0.223 ± 0.012 | 0.219 ± 0.008 | 0.220 ± 0.008 |
| EXN2 | 0.226 ± 0.008 | 0.225 ± 0.010 | 0.224 ± 0.006 | 0.224 ± 0.008 | 0.224 ± 0.005 |
| EXN3 | 0.217 ± 0.010 | 0.219 ± 0.009 | 0.220 ± 0.008 | 0.221 ± 0.006 | 0.220 ± 0.008 |
| EXN4 | 0.224 ± 0.010 | 0.224 ± 0.008 | 0.222 ± 0.006 | 0.222 ± 0.005 | 0.222 ± 0.006 |

As is apparent from Table 5, the testosterone level in the intact rats during a course of treatment demonstrates significant changes in groups EXN2-EXN4, i.e., precisely in those groups where the compounds corresponding to the present invention were tested. The maximum increases in testosterone (18.3%, 19.3% and 26.0% respectively at p<0.01 corresponded to termination of the course of treatment in which a significant delayed effect was still observed after 20 days. The rise in testosterone induced a rise in the progesterone level, which increased and maintained a dynamic similar to that of testosterone but more intensely, which might be associated with activation of adrenal activity. The maximum increase was 22.9%, 31.6% and 39.8% respectively at p<0.01. Significant changes in estradiol and dehydroepiandosterone levels were not noted.

TABLE 6

Level of hormones in blood and hypogonadal rats during a course of treatmen twith the compound and after termination of treatment.

| Group | Day 0 | Day 5 | Day 10 | Day 20 | Day 30 |
|---|---|---|---|---|---|
| Testosterone, nmol/L | | | | | |
| KN | 4.02 ± 0.59 | 3.97 ± 0.62 | 4.01 ± 0.56 | 4.06 ± 0.46 | 4.04 ± 0.56 |
| EXG1 | 4.11 ± 0.68 | 4.49 ± 0.66 | 4.48 ± 0.42 | 4.11 ± 0.68 | 4.12 ± 0.66 |
| EXG2 | 4.06 ± 0.52 | 5.01 ± 0.94 | 5.08 ± 0.78 | 4.96 ± 0.52 | 4.88 ± 0.62 |
| EXG3 | 4.01 ± 0.84 | 5.21 ± 1.06 | 5.46 ± 0.88 | 5.30 ± 0.48 | 5.26 ± 0.40 |
| EXG4 | 3.99 ± 0.72 | 5.76 ± 1.22 | 5.74 ± 0.52 | 5.65 ± 0.47 | 5.12 ± 0.44 |
| Progesterone, nmol/L | | | | | |
| KN | 5.19 ± 0.56 | 5.15 ± 0.72 | 5.13 ± 0.63 | 5.18 ± 0.59 | 5.17 ± 0.66 |
| EXG1 | 5.22 ± 0.73 | 5.40 ± 0.97 | 5.37 ± 0.92 | 5.30 ± 0.78 | 5.32 ± 0.47 |
| EXG2 | 5.15 ± 0.46 | 5.58 ± 0.97 | 5.62 ± 0.77 | 5.47 ± 0.64 | 5.34 ± 0.44 |
| EXG3 | 5.21 ± 0.37 | 5.74 ± 0.86 | 5.80 ± 0.87 | 5.61 ± 0.56 | 5.42 ± 0.62 |
| EXG4 | 5.23 ± 0.58 | 5.78 ± 0.67 | 5.86 ± 0.98 | 5.66 ± 0.76 | 5.61 ± 0.46 |
| Estradiol, nmol/L | | | | | |
| KN | 0.50 ± 0.04 | 0.48 ± 0.06 | 0.50 ± 0.03 | 0.49 ± 0.05 | 0.49 ± 0.04 |
| EXG1 | 0.49 ± 0.05 | 0.49 ± 0.05 | 0.50 ± 0.06 | 0.50 ± 0.06 | 0.50 ± 0.04 |
| EXG2 | 0.51 ± 0.06 | 0.50 ± 0.06 | 0.49 ± 0.06 | 0.49 ± 0.06 | 0.49 ± 0.05 |
| EXG3 | 0.48 ± 0.07 | 0.49 ± 0.09 | 0.48 ± 0.06 | 0.50 ± 0.08 | 0.49 ± 0.06 |
| EXG4 | 0.51 ± 0.05 | 0.50 ± 0.07 | 0.51 ± 0.06 | 0.51 ± 0.06 | 0.50 ± 0.06 |
| Dehydroepiandosterone sulfate, μg/mL | | | | | |
| KN | 0.218 ± 0.010 | 0.217 ± 0.009 | 0.218 ± 0.009 | 0.218 ± 0.008 | 0.219 ± 0.008 |
| EXG1 | 0.220 ± 0.008 | 0.222 ± 0.012 | 0.222 ± 0.012 | 0.220 ± 0.009 | 0.219 ± 0.006 |
| EXG2 | 0.221 ± 0.008 | 0.221 ± 0.009 | 0.220 ± 0.012 | 0.220 ± 0.008 | 0.221 ± 0.010 |
| EXG3 | 0.219 ± 0.012 | 0.220 ± 0.008 | 0.219 ± 0.006 | 0.219 ± 0.006 | 0.220 ± 0.006 |
| EXG4 | 0.221 ± 0.012 | 0.222 ± 0.010 | 0.222 ± 0.009 | 0.221 ± 0.006 | 0.221 ± 0.006 |

As is apparent from Table 6, the low level of testosterone in the hypogonadal rats actively increases in the groups in which the compounds according to examples 2-4 were used. Relative to the base level the maximum increases was 25.1%, 36.2% and 43.9% at p<0.01. It is particularly important that the tested compounds according to examples 2, 3 and 4 brought the testosterone level in the hypogonadal rats almost to the level of the intact animals.

Progesterone also rose significantly, but not as significantly. The estradiol and dehydroepiandosterone levels did not change significantly.

TABLE 7

Level of hormones in blood of intact rats during a single (acute) taking of the compound 2 hours after taking.

| Group | Testosterone, nmol/L | | Progesterone, nmol/L | | Estradiol, nmol/L | | Dehydroepi-androsterone, µg/mL | |
|---|---|---|---|---|---|---|---|---|
| | before | after | before | after | before | after | before | after |
| K | 5.83 ± 0.66 | 5.81 ± 0.58 | 4.27 ± 0.46 | 4.26 ± 0.56 | 0.66 ± 0.06 | 0.66 ± 0.05 | 0.222 ± 0.008 | 0.222 ± 0.006 |
| EXN1 | 5.82 ± 0.48 | 5.96 ± 0.87 | 4.26 ± 0.56 | 4.31 ± 0.82 | 0.65 ± 0.08 | 0.64 ± 0.08 | 0.219 ± 0.009 | 0.220 ± 0.012 |
| EXN2 | 5.77 ± 0.54 | 6.10 ± 0.68 | 4.22 ± 0.60 | 4.51 ± 0.73 | 0.63 ± 0.11 | 0.62 ± 0.09 | 0.218 ± 0.014 | 0.219 ± 0.010 |
| EXN3 | 5.80 ± 0.67 | 6.14 ± 0.49 | 4.28 ± 0.48 | 4.69 ± 0.86 | 0.64 ± 0.12 | 0.64 ± 0.10 | 0.220 ± 0.010 | 0.221 ± 0.009 |
| EXN4 | 5.77 ± 0.49 | 6.29 ± 0.82 | 4.26 ± 0.62 | 4.88 ± 1.03 | 0.65 ± 0.08 | 0.59 ± 0.07 | 0.220 ± 0.008 | 0.221 ± 0.010 |

It is apparent from Table 7 that the actual increase in testosterone level is ensured by the compounds according to examples 2, 3 and 4. The level of increase was 5.7%, 5.9% and 9.0% respectively but only in group EXN4 at p<0.01. An increase in progesterone in the same groups is also traced in this trend. The estradiol and dehydroepiandosterone levels did not change significantly.

TABLE 8

Level of hormones in blood of hypogonadal rats during single (acute) administraton of the compound 2 hours after administration

| Group | Testosterone, nmol/L | | Progesterone, nmol/L | | Estradiol, nmol/L | | Dehydroepi-androsterone, µg/mL | |
|---|---|---|---|---|---|---|---|---|
| | before | after | before | after | before | after | before | after |
| KN | 4.06 ± 0.53 | 4.00 ± 0.62 | 5.26 ± 0.74 | 5.22 ± 0.66 | 0.55 ± 0.16 | 0.54 ± 0.09 | 0.218 ± 0.009 | 0.218 ± 0.010 |
| EXG1 | 4.01 ± 0.22 | 4.17 ± 0.74 | 5.19 ± 0.65 | 5.27 ± 0.70 | 0.51 ± 0.09 | 0.50 ± 0.11 | 0.224 ± 0.014 | 0.222 ± 0.012 |
| EXG2 | 3.97 ± 0.64 | 4.51 ± 0.76 | 5.20 ± 0.55 | 5.68 ± 0.76 | 0.53 ± 0.10 | 0.53 ± 0.08 | 0.220 ± 0.012 | 0.220 ± 0.009 |
| EXG3 | 4.08 ± 0.98 | 4.77 ± 0.86 | 5.24 ± 0.59 | 5.75 ± 0.66 | 0.54 ± 0.09 | 0.55 ± 0.08 | 0.219 ± 0.008 | 0.219 ± 0.007 |
| EXG4 | 4.11 ± 0.46 | 4.97 ± 0.69 | 5.16 ± 0.38 | 5.78 ± 0.50 | 0.52 ± 0.06 | 0.53 ± 0.06 | 0.221 ± 0.012 | 0.222 ± 0.010 |

It is apparent from Table 8 that the compound according to example 1 exhibits an insignificant increase in testosterone and progesterone, whereas the compounds according to examples 2, 3 and 4 exhibit a significant increase in testosterone of 13.6%, 16.1% and 20.9% at p<0.01 and an increase in progesterone within this trend. The estradiol and dehydroepiandosterone levels did not change.

Rats are mammals with a year-round reproductive cycle, similar to humans. Male rats have a spermatogenesis and arousal mechanism that is similar to humans, and females have a defined ovulatory cycle. Thus, the rat model is recognized as being sufficiently close to the human model, see, e.g., F. H. de Jonge, E. M. Eerland, N. E. van de Poll, *The influence of estrogen, testosterone and progesterone on partner preference, receptivity and proceptivity*, Physiol. Behav. 37(6):885-91 (1986).

Example 6

Primary selection of human patients was conducted with the ADAM test (Androgen Deficiency in Aging Males questionnaire):

First symptom of testosterone deficiency—Are you experiencing a reduction in sexual activity?

Second symptom of testosterone deficiency—Are you feeling a lack of energy?

Third symptom of testosterone deficiency—Are you experiencing a reduction in strength and endurance?

Fourth symptom of testosterone deficiency—Has your height diminished?

Fifth symptom of testosterone deficiency—Are you noticing a reduction in "enjoyment of life"?

Sixth symptom of testosterone deficiency—Are you subject to a feeling of melancholy and irritability?

Seventh symptom of testosterone deficiency—Have your erections become less strong?

Eighth symptom of testosterone deficiency—Have you recently noticed a reduction in capacity to engage in sports?

Ninth symptom of testosterone deficiency—Do you feel a need to sleep after meals?

Tenth symptom of testosterone deficiency—Have you recently noticed a deterioration in work capacity?

An affirmative answer to the first or seventh question or to any three other questions creates the suspicion of testosterone deficiency.

Men who took the test with a positive result were asked to undergo blood analysis. Blood was sampled no later than 2 hours after waking. This is associated with nonuniformity of testosterone concentration in the blood during the day. The maximum pertains to the morning hours and the fluctuations are up to 35%, sometimes even 50%.

Normally the testosterone level in males is 2.5-5.3 ng/mL. In the morning hours, a value below 2.8 ng/mL is considered a reduced testosterone level. The following factors were the criterion for selection of the groups of subjects:

testosterone level below 2.8 ng/m;
age 40 to 60 years;
absence of drug addiction or alcoholism;
absence of oncological disease.

A consent form was signed by all volunteers.

Five groups of 26 men each were formed with a random number generator.

Owing to the small number of volunteers the clinical study was conducted in two stages.

First stage—single taking of the compound.

Control (K)—placebo group. The patients took on waking five size number 3 capsules filled with cornstarch.

Experiment 1 (O1)—experimental group, which received five tablets of the agent according to example 1 on waking.

Experiment 2 (O2)—experimental group, which received five tablets of the agent according to example 2 on waking.

Experiment 3 (O3)—experimental group, which received seven coated tablets of the agent according to example 3 on waking.

Experiment 4 (O4)—experimental group who received on waking four sets of capsules of the agent according to example 4.

Blood was taken from the patients of the different groups in different rooms.

The first sample was taken on the evening before taking the compound and the second on the next day 2 hours after the morning administration.

Method of determination: The type and amount of testosterone from the investigated serum was determined by bonding with primary monoclonal antibodies to the given hormone. The monoclonal antibodies were obtained from AlkorBio, http:**www.english.alkorbio.ru/. The primary monoclonal antibodies were applied to the surface of the well. Secondary monoclonal antibodies to the hormone conjugated with horseradish peroxidase react with the primary monoclonal antibodies. The type and the amount of the appropriate hormone in the analyzed serum or monoclonal antibody was determined by binding the first monoclonal antibodies to that hormone. The primary monoclonal antibodies were applied to the surface of the wells. The primary monoclonal antibodies and the secondary monoclonal antibodies react to the hormone, which are conjugated with the horseradish peroxidase. As a result a "sandwich" type complex is formed. The linked substrate (enzyme, hormone) is quantified by a color reaction with a chromogenic substrate. The color intensity is proportional to the concentration of the defined hormone in the sample. Calculations are performed automatically using a multichannel spectrophotometer "Uniplan" (Russia) at a wavelength of 450 nm.

As a result, a complex of the sandwich type is formed. The bound substrate (enzyme, hormone) is determined quantitatively by color reaction with a chromogenic substrate. The intensity of the color is proportional to the concentration of the investigated hormone in the sample. The results are calculated automatically with multichannel recording spectrophotometer at a wavelength of 450 nm.

TABLE 9

Testosterone level of the blood during a single morning administration.

| Group | Testosterone level, ng/mL | | Increase, % |
|---|---|---|---|
| | Before administration | After administration | |
| K | 2.26 ± 0.28 | 2.46 ± 0.39 | +8.8 |
| O1 | 2.31 ± 0.56 | 2.75 ± 0.62 | +19.0 ($p = 0.05$) |
| O2 | 2.28 ± 0.46 | 2.93 ± 0.68 | +28.5 ($p < 0.01$) |
| O3 | 2.23 ± 0.67 | 3.06 ± 0.84 | +37.2 ($p < 0.01$) |
| O4 | 2.29 ± 0.28 | 3.18 ± 0.92 | +38.9 ($p < 0.01$) |

Table 9 demonstrates that during a single taking in men, the placebo effect has a very significant effect on the free testosterone level of the blood. For this reason, in performing the calculations to correct for the placebo effect, use of the compound according to example 1 loses its significance and the effect is lowered to merely a tendency, whereas the effect from using the agents according to examples 2, 3 and 4 retains its significance ($p<0.01$) and amounts to 20-30%.

Example 7

Course of treatment with the compound.

Owing to the small number of volunteers the course of treatment was conducted in the same groups as in example 6. Originally the plan was to change the compound in each group, but owing to the different commercial forms of the compounds, this was not possible. Grinding to powders also prove useless, owing to the different color and odor of the compounds.

Control (K)—placebo group. The patients received daily at 10:00 a.m. and 5:00 p.m. one capsule no. 3 for 10 days, filled with cornstarch.

Experiment 1 (O1)—experimental group, which received tablets of the agents according to example 1 for 10 days daily at 10:00 a.m. and 5:00 p.m. two tablets each.

Experiment 2 (O2)—experimental group, which received tablets of the agents according to example 2 for 10 days daily at 10:00 a.m. and 5:00 p.m. two tablets each.

Experiment 3 (O3)—experimental group, which received a coated tablet of the agent according to example 3 for 10 days daily at 10:00 a.m. and 5:00 p.m., one coated tablets each.

Experiment 4 (O4)—experimental group, which received daily the set of agents according to example 4 at 10:00 a.m. and 5:00 p.m.

In all groups, blood analysis was performed 5 days before the beginning of the study (point −5), on the morning of the first day before taking the compound (point 0), on the morning of the fifth day before taking the compound (point 5), on the morning of the tenth day before taking the compound (point 10), on the morning of the tenth after termination of taking (point 20), on the morning of the twentieth day after termination of taking (point 30).

TABLE 10

Testosterone level of the blood during a course of treatment.

| | Testosterone level, ng/mL | | | | | | Maximum increase, % |
|---|---|---|---|---|---|---|---|
| | −5 | 0 | 5 | 10 | 20 | 30 | |
| K | 2.34 ± 0.47 | 2.29 ± 0.76 | 2.40 ± 0.68 | 2.34 ± 0.63 | 2.30 ± 0.87 | 2.29 ± 0.53 | |
| O1 | 2.33 ± 0.56 | 2.31 ± 0.42 | 2.39 ± 0.78 | 2.88 ± 0.90 | 2.36 ± 0.72 | 2.35 ± 0.45 | +23.6 |
| O2 | 2.29 ± 0.43 | 2.28 ± 0.38 | 3.22 ± 0.97 | 4.05 ± 0.67 | 3.81 ± 0.60 | 3.61 ± 0.48 | +77.6 |
| O3 | 2.23 ± 0.36 | 2.32 ± 0.54 | 3.40 ± 0.48 | 4.60 ± 0.66 | 4.38 ± 0.84 | 3.98 ± 0.45 | +98.3 |
| O4 | 2.29 ± 0.26 | 2.30 ± 0.56 | 3.56 ± 0.43 | 4.67 ± 0.67 | 4.42 ± 0.47 | 4.22 ± 0.55 | +103.0 |

Note: The maximum testosterone level is shown in the 10 day column, points O2, O3, O4. The increase is defined as the ratio of maximum testosterone level to the value of point 0.

On the 20th day after completion of the treatment (point 30) the patients underwent the ADAM test again. The following results were obtained:

Group K—11 patients did not pass the test.

Group O1—7 patients did not pass the test.

Groups O2, O3 and O4—all patients passed the test.

The attained results suggest that the agent according to example 1 only ensured partial remission of impotence, whereas the compounds according to examples 2, 3 and 4 ensured a 100% remission, which is a significant result.

No contraindications were found during the study. No conflict with other drugs or food was found. Complaints of deterioration in physical or psychoemotional state did not occur.

Having thus described a preferred embodiment, it should be apparent to those skilled in the art that certain advantages of the described method have been achieved.

It should also be appreciated that various modifications, adaptations, and alternative embodiments thereof may be made within the scope and spirit of the present invention. The invention is further defined by the following claims.

LITERATURE

1. D. Bitran, E. Hull, *Pharmacological analysis of male rat sexual behavior*, Neurosci. Biobehav. Rev., vol. 11, pp. 365-89 (1987).
2. A. I. Gladkova, *Role of neurotransmitters in coordination of male sexual behavior*, Neurophysiology, vol. 32, no. 1, pp. 69-74 (2000).

We claim:

1. A non-steroidal composition for regulating male sexual function, comprising:
    at least one amino acid in an amount of 1-1000 mg and selected from a group consisting of L-Glutamic acid (glutamate), L-Arginine, glycine, L-aspartate, L-carnitine, L-tyrosine, L-glutamine, monosodium-L-glutamate monohydrate, L-potassiumarginine, L-ammoniumaspartate, L-arginine HCl, sodium-L-tyrosine, and lithium aspartate;
    at least one vitamin, in the amount of 1-500% of a daily recommended dose; and
    at least one chelated compound of a formula: R1-Me-R2.nH$_2$O,
    wherein Me is a metal chosen from any of Ca, Mg and Zn,
    wherein R1 is a dicarboxylic acid anion chosen from a group consisting of succinic acid, fumaric acid or aspartic acid,
    wherein R2 is a dicarboxylic acid anion chosen from the group consisting of succinic acid, fumaric acid or aspartic acid,
    wherein R1 is the same as R2, and
    wherein n=0-8.

2. The composition of claim 1, further comprising at least one monoammonium and/or diammonium salt of a dicarboxylic acid chosen from succinic or fumaric acid, in the amount of 20-5000 mg.

3. The composition of claim 1, wherein the composition increases testosterone level in pathologies that cause suppression of testosterone synthesis, including hypogonadism.

4. The composition of claim 1, further comprising any of (i) sugar, (ii) starch, (iii) casein, (iv) microcellulose, (v) inert compounds, including any of dry mil, activated coal, flour and fillers, (vi) calcium stearate, (vii) stearic acid, (viii) magnesium stearate, (ix) talcum, and (x) mixture of (i)-(ix) as excipients.

5. The composition of claim 1, wherein the composition increases testosterone level in a body of a male mammal.

6. The composition of claim 1, wherein the composition is in a form of a powder, granules, tablets or capsules.

7. The composition of claim 5, wherein the composition is in a form of a set of two powders, granules, tablets or capsules.

8. A method for regulating male sexual function, the method comprising:
    providing a single administration of 100-20000 mg of a composition of claim 1.

9. The method of claim 7, further comprising providing a course of treatment lasting from 3 to 90 days with daily taking of 10-20,000 mg of the composition one or more times.

10. The method of claim 8, wherein a number of courses is unlimited.

11. The composition of claim 1, wherein Me is Ca or Mg.

12. The composition of claim 1, wherein Me is Ca.

13. The composition of claim 1, wherein Me is Mg.

14. The composition of claim 1, wherein the at least one amino acid is selected from a group consisting of L-Glutamic acid (glutamate), glycine, L-aspartate, L-tyrosine, L-glutamine, monosodium-L-glutamate monohydrate, L-potassiumarginine, L-ammoniumaspartate, and sodium-L-tyrasine, and lithium aspartate.

15. A non-steroidal composition for regulating male sexual function, comprising:
    at least one amino acid in an amount of 1-1000 mg and selected from a group consisting of L-Glutamic acid (glutamate), L-Arginine, glycine, L-aspartate, L-carnitine, L-tyrosine, L-glutamine, monosodium-L-glutamate monohydrate, L-potassiumarginine, L-ammoniumaspartate, L-arginine HCl, sodium-L-tyrosine and lithium aspartate;
    at least one vitamin, in the amount of 1- 500% of a daily recommended dose; and
    at least one chelated compound R1-Ca—R2.nH$_2$O,
    wherein R1 is succinic acid, fumaric acid or aspartic acid,
    wherein R2 is succinic acid, fumaric acid or aspartic acid,
    wherein R1 is the same as R2, and
    wherein n is no greater than 8.

* * * * *